(12) United States Patent
Fischvogt

(10) Patent No.: US 8,911,463 B2
(45) Date of Patent: Dec. 16, 2014

(54) BLADED/BLADELESS OBTURATOR FOR USE IN A SURGICAL TROCAR ASSEMBLY

(75) Inventor: Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 889 days.

(21) Appl. No.: 12/432,913

(22) Filed: Apr. 30, 2009

(65) Prior Publication Data

US 2009/0306697 A1    Dec. 10, 2009

Related U.S. Application Data

(60) Provisional application No. 61/060,147, filed on Jun. 10, 2008.

(51) Int. Cl.
*A61B 17/34* (2006.01)
*A61B 18/14* (2006.01)

(52) U.S. Cl.
CPC ......... *A61B 17/3496* (2013.01); *A61B 17/3421* (2013.01); *A61B 17/3474* (2013.01); *A61B 18/1487* (2013.01); *A61B 2017/3456* (2013.01)
USPC ...................................................... 606/185

(58) Field of Classification Search
CPC ........... A61B 17/3494; A61B 17/3496; A61B 17/34; A61B 17/3415; A61B 17/3417
USPC ........ 606/167, 185, 170; 604/164.01, 164.02, 604/167.01, 167.03, 167.06, 264, 170.02
See application file for complete search history.

(56) References Cited

U.S. PATENT DOCUMENTS

| | | | |
|---|---|---|---|
| 4,535,773 | A | 8/1985 | Yoon |
| 4,601,710 | A | 7/1986 | Moll |
| 4,654,030 | A | 3/1987 | Moll et al. |
| 4,902,280 | A | 2/1990 | Lander |
| 4,931,042 | A | 6/1990 | Holmes et al. |
| 5,030,206 | A | 7/1991 | Lander |
| 5,066,288 | A | 11/1991 | Deniega et al. |
| 5,104,382 | A | 4/1992 | Brinkerhoff et al. |
| 5,114,407 | A | 5/1992 | Burbank |
| 5,116,353 | A | 5/1992 | Green |
| 5,127,909 | A | 7/1992 | Shichman |

(Continued)

FOREIGN PATENT DOCUMENTS

EP    0 604 197 A2    12/1993
EP    0 617 924 A2    2/1994

(Continued)

OTHER PUBLICATIONS

European Search Report for corresponding EP 09251393 date of mailing is Oct. 6, 2009 (4 pages).

*Primary Examiner* — Thomas McEvoy

(57) ABSTRACT

An obturator assembly is provided and generally includes an obturator housing and a support tube extending distally from the obturator housing. A shield nose is affixed to a distal end of the support tube. The shield nose defines a truncated cavity and having a concave center portion. An obturator member is movably mounted relative to the support tube. A cutting blade is provided having at least one cutting edge and is affixed to a distal end of the obturator member. The cutting blade is movable within the truncated cavity. The shield nose has at least one slot formed through the concave center portion and in communication with the truncated cavity for allowing passage of the at least one cutting edge therethrough.

19 Claims, 8 Drawing Sheets

(56) References Cited

U.S. PATENT DOCUMENTS

| | | | |
|---|---|---|---|
| 5,152,754 A | 10/1992 | Plyley et al. |
| 5,158,552 A | 10/1992 | Borgia et al. |
| 5,215,526 A | 6/1993 | Deniega et al. |
| 5,226,426 A | 7/1993 | Yoon |
| 5,246,425 A | 9/1993 | Hunsberger et al. |
| 5,248,298 A | 9/1993 | Bedi et al. |
| 5,263,937 A | 11/1993 | Shipp |
| 5,275,583 A | 1/1994 | Crainich |
| 5,290,243 A | 3/1994 | Chodorow et al. |
| 5,295,993 A | 3/1994 | Green |
| 5,312,354 A | 5/1994 | Allen et al. |
| 5,314,417 A | 5/1994 | Stephens et al. |
| 5,318,580 A | 6/1994 | Gresl, Jr. |
| 5,318,585 A | 6/1994 | Guy et al. |
| 5,338,305 A | 8/1994 | Plyley et al. |
| 5,346,459 A | 9/1994 | Allen |
| 5,350,393 A | 9/1994 | Yoon |
| 5,356,421 A | 10/1994 | Castro |
| 5,364,365 A | 11/1994 | Wortrich |
| 5,364,372 A | 11/1994 | Danks et al. |
| 5,370,625 A | 12/1994 | Shichman |
| 5,372,588 A | 12/1994 | Farley et al. |
| 5,387,197 A | 2/1995 | Smith et al. |
| 5,399,167 A | 3/1995 | Deniega |
| 5,411,515 A | 5/1995 | Haber et al. |
| 5,417,705 A | 5/1995 | Haber et al. |
| 5,423,848 A | 6/1995 | Washizuka et al. |
| 5,431,635 A | 7/1995 | Yoon |
| 5,437,643 A | 8/1995 | Transue |
| 5,441,513 A | 8/1995 | Roth |
| 5,462,532 A | 10/1995 | Gresl |
| 5,474,539 A | 12/1995 | Costa et al. |
| 5,486,190 A | 1/1996 | Green |
| 5,522,833 A | 6/1996 | Stephens et al. |
| 5,527,335 A | 6/1996 | Bolduc et al. |
| 5,538,509 A | 7/1996 | Dunlap et al. |
| 5,549,564 A | 8/1996 | Yoon |
| 5,578,053 A | 11/1996 | Yoon |
| 5,584,848 A * | 12/1996 | Yoon .......................... 606/185 |
| 5,591,186 A | 1/1997 | Wurster et al. |
| 5,591,190 A | 1/1997 | Yoon |
| 5,607,440 A | 3/1997 | Danks et al. |
| 5,626,598 A | 5/1997 | Roth |
| 5,645,556 A | 7/1997 | Yoon |
| 5,645,557 A | 7/1997 | Yoon |
| 5,669,885 A | 9/1997 | Smith |
| 5,674,237 A | 10/1997 | Ott |
| 5,676,156 A | 10/1997 | Yoon |
| 5,697,947 A | 12/1997 | Wolf et al. |
| 5,772,660 A | 6/1998 | Young et al. |
| 5,779,680 A | 7/1998 | Yoon |
| 5,827,315 A | 10/1998 | Yoon |
| 5,843,115 A * | 12/1998 | Morejon .......................... 606/185 |
| 5,851,216 A | 12/1998 | Allen |
| 5,860,996 A | 1/1999 | Urban et al. |
| 5,868,773 A | 2/1999 | Danks et al. |
| 5,904,699 A | 5/1999 | Schwemberger et al. |
| 5,980,493 A | 11/1999 | Smith et al. |
| 5,984,941 A | 11/1999 | Wilson et al. |
| 6,017,356 A | 1/2000 | Frederick et al. |
| 6,036,711 A | 3/2000 | Mozdzierz et al. |
| 6,077,284 A | 6/2000 | Piraka |
| 6,099,544 A | 8/2000 | Wolf et al. |
| 6,270,501 B1 | 8/2001 | Freiberg et al. |
| 6,296,651 B1 | 10/2001 | Lary et al. |
| 6,319,266 B1 | 11/2001 | Stellon et al. |
| 6,478,806 B2 | 11/2002 | McFarlane |
| 6,837,874 B1 | 1/2005 | Popov |
| 6,884,253 B1 | 4/2005 | McFarlane |
| 7,367,960 B2 | 5/2008 | Stellon et al. |
| 2002/0143236 A1 | 10/2002 | Sauer et al. |
| 2006/0226655 A1* | 10/2006 | Smith .......................... 285/401 |
| 2007/0005087 A1* | 1/2007 | Smith et al. .......................... 606/185 |

FOREIGN PATENT DOCUMENTS

| | | |
|---|---|---|
| EP | 1738700 | 1/2007 |
| WO | WO 94/22508 | 3/1994 |
| WO | WO 0102123 A | 3/2001 |
| WO | WO 01/34228 | 5/2001 |
| WO | WO 02/11605 | 2/2002 |
| WO | WO 2007/035889 A | 3/2007 |

\* cited by examiner

BLADED/BLADELESS OBTURATOR FOR USE IN A SURGICAL TROCAR ASSEMBLY

CROSS REFERENCE TO RELATED APPLICATION

The present application claims the benefit of and priority to U.S. Provisional Application Ser. No. 61/060,147 filed on Jun. 10, 2008, the entire contents of which are incorporated herein by reference.

BACKGROUND

1. Technical Field

The present disclosure relates to an obturator assembly for use in a surgical trocar assembly. More particularly, the present disclosure relates to an obturator assembly having a bladeless tip and a retractable bladed cutting surface within the bladeless tip.

2. Background of Related Art

Minimally invasive procedures are continually increasing in number and variation. Forming a relatively small diameter, temporary pathway to the surgical site is a key feature of most minimally invasive surgical procedures. The most common method of providing such a pathway is by inserting a trocar assembly through the skin. Common trocar assemblies generally include an obturator assembly for penetrating the skin and a cannula assembly for providing a sealed passageway for insertion of surgical instruments into a body cavity. In many procedures, the trocar assembly is inserted into a body cavity of a patient and the body cavity is insufflated to provide a working space. Upon removal of the obturator assembly, the cannula assembly is utilized to provide the necessary pathway to the surgical site while minimizing leakage of insufflation gases.

The obturator assembly may include a safety shield which protects against unintentional puncturing by a sharpened tip of the obturator assembly. One example of a safety shield mechanism is disclosed in commonly assigned U.S. Pat. No. 6,319,266 to Stellon et al., the entire disclosure of which is incorporated by reference herein.

During certain particularly delicate operations care is required to prevent underlying organs from being punctured by the sharpened tip of the obturator assembly. Therefore, it is desirable to provide an obturator assembly which includes multiple safety mechanisms to prevent engagement of the sharpened tip of the obturator assembly with the underlying organs. It is further desirable to provide an obturator assembly having an obturator member and cutting blade which may be manually advanced to expose the cutting blade to tissue.

SUMMARY

An obturator assembly is provided and generally includes an obturator housing and a support tube extending distally from the obturator housing. A shield nose is affixed to a distal end of the support tube. The shield nose defines a truncated cavity and includes a concave center portion. An obturator member is movably mounted relative to the support tube. A cutting blade is provided having at least one cutting edge and is affixed adjacent a distal end of the obturator member. The cutting blade is movable within the truncated cavity. The shield nose has at least one slot, formed through the concave center portion, in communication with the truncated cavity for allowing passage of the at least one cutting edge therethrough. The shield nose has a blunt tip distal of the truncated cavity. The truncated cavity includes a planner portion for receipt of the cutting blade. The truncated cavity also includes a cylindrical portion for receipt of the distal end of the obturator member.

A spring is positioned between the obturator housing and the obturator member to bias the obturator member proximally relative to the support tube. A plunger is affixed to a proximal end of the obturator member to manually move the obturator member relative to the support tube.

In one embodiment, an electrical conduit is attached to the obturator housing and is in electrical connection with the cutting blade to provide electrocautery features to the cutting blade. In a specific embodiment, the obturator member is formed of an electrically conductive material. In an alternative specific embodiment, the obturator member is formed of an electrically nonconductive material and includes an electrically conductive inner core in electrical contact with the cutting blade.

There is also disclosed an obturator assembly generally including an obturator housing, a support tube extending distally from the obturator housing and a shield nose affixed to a distal end of the support tube, the shield nose defining a cavity. An obturator member is movably mounted relative to the support tube. A cutting blade, having at least one cutting edge, is affixed to a distal end of the obturator member. The cutting blade is movable within the cavity. The obturator assembly further includes a safety shield movably mounted to the obturator housing.

A spring is provided and is engageable with the safety shield to bias the safety shield distally relative to the obturator housing. A driver is engageable with the spring and is affixed to a proximal end of the safety shield.

In one embodiment, a guide is formed in the obturator housing and a tab is formed on the driver and is movable within the guide. In a specific embodiment, the shield nose has a concave center portion and at least one slot formed through the concave center portion and in communication therewith for allowing passage of the at least one cutting edge therethrough.

There is also disclosed a trocar assembly generally including a cannula assembly having a cannula housing and a cannula sleeve extending distally from the cannula housing and an obturator assembly insertable through the cannula assembly. The obturator assembly includes an obturator housing and a support tube extending distally from the obturator housing. A shield nose is affixed to a distal end of the support tube and defines a cavity. An obturator member is movably mounted relative to the support tube. A cutting blade having at least one cutting edge is provided and is affixed to a distal end of the obturator member. The cutting blade is movable within the cavity. The disclosed trocar assembly further includes a safety shield movably mounted to the obturator housing.

The cannula housing includes a valve positioned within an interior of the cannula housing such that the valve seals about the safety shield when the obturator assembly is inserted into the cannula assembly.

DESCRIPTION OF THE DRAWINGS

An embodiment of the presently disclosed trocar assembly is disclosed herein with reference to the drawings, wherein:

FIG. 3b is a cross-sectional view taking along line 3b-3b of FIG. 3a;

DETAILED DESCRIPTION OF EMBODIMENTS

An embodiment of the presently disclosed obturator assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
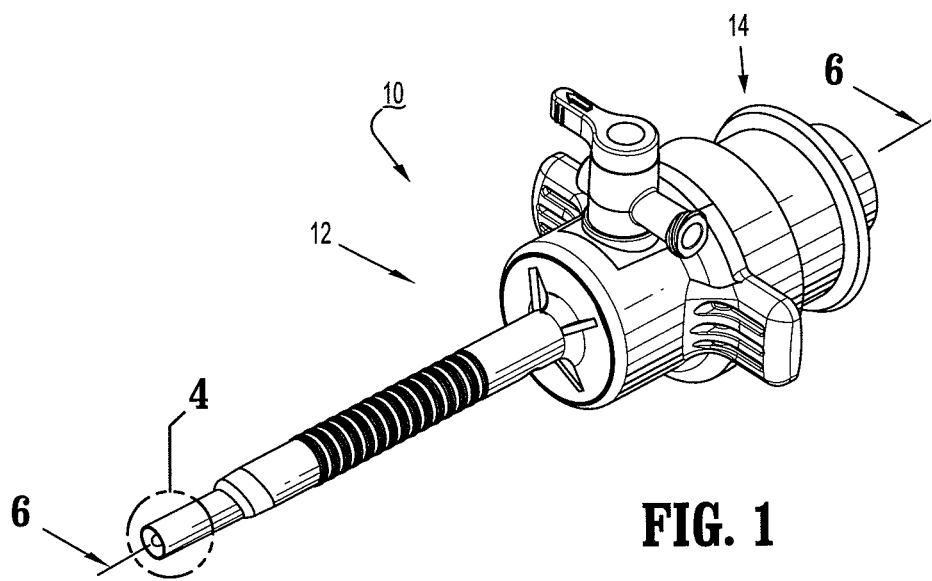
FIG. 1 is a perspective view of the disclosed trocar assembly including an obturator assembly and a cannula assembly.
Figure 2:
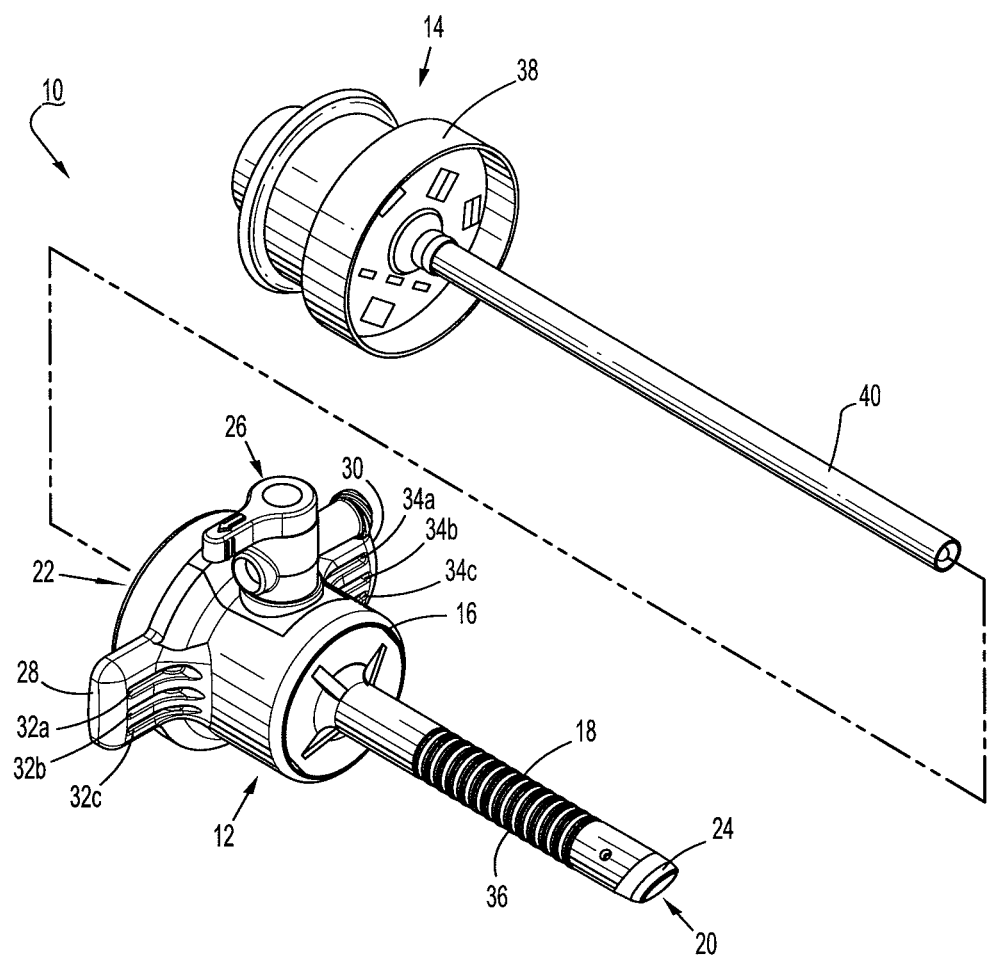
FIG. 2 is a perspective view of the disclosed trocar assembly with the obturator assembly separated from the cannula assembly.

Referring to FIGS. 1 and 2, there is disclosed a trocar assembly 10 including a cannula assembly 12 and an obturator assembly 14 positioned through cannula assembly 12. Cannula assembly 12 provides an access port for various surgical instruments into the body as well as a conduit for a source of insufflation fluid to insufflate the body to create a working cavity.

With reference to FIG. 2, cannula assembly 12 includes a cannula housing 16 and elongate cannula sleeve 18 extending distally from cannula housing 16. Cannula housing 16 and cannula sleeve 18 define a throughbore 20 which extends from a proximal end 22 of cannula housing 16 to a distal end 24 of cannula sleeve 18. A check valve 26 is provided on cannula housing 16 to receive a source of insufflation fluid for passage into the body of a patient. Cannula housing 16 is additionally provided with a pair of suture wings 28 and 30 to facilitate securing cannula assembly 12 to the body of a patient. Specifically, suture wings 28 and 30 include respective slots 32a-c and 34a-c for receipt of lengths of suture material to secure cannula assembly 12 to the patient's body.

Obturator assembly 14 generally includes an obturator housing 38 and an elongate safety shield 40 extending distally from, and movably mounted within, obturator housing 38. Safety shield 40 is provided to automatically cover a cutting device associated with obturator assembly 14 (as described in more detail hereinbelow) once the cutting device has penetrated the body of a patient to prevent puncturing of underlying organs the wall of the patient punctured.

Figure 3:
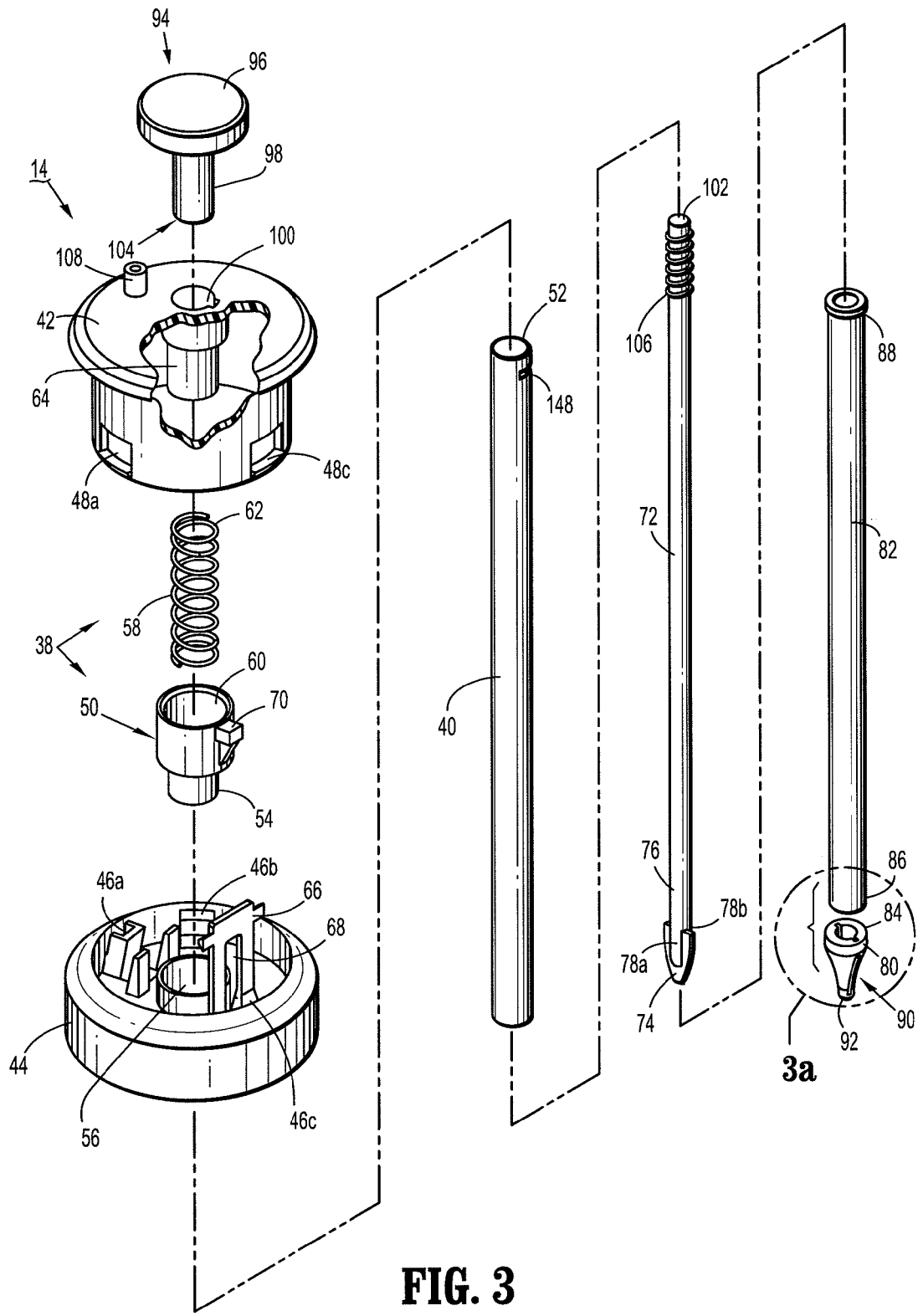
FIG. 3 is perspective view, with parts separated, of the disclosed obturator assembly.

Referring now to FIG. 3, obturator housing 38 includes an upper housing 42 and a lower housing 44. A plurality of tabs 46a-c are provided on lower housing 44 and engage a corresponding plurality of slots 48a-c to hold upper housing and 42 and lower housing 44 together. As noted hereinabove, safety shield 40 is movably mounted within obturator housing 38. A driver 50 is movably mounted within upper housing 42 and lower housing 44 and is affixed to a proximal end 52 of safety shield 40. Specifically, a distal end 54 of driver 50 is affixed to proximal end 52 of safety shield 40 (see FIG. 8). Safety shield 40 passes through a hole 56 formed in lower housing 44. A spring 58 is provided within obturator housing 38 to bias safety shield 40 distally relative to obturator housing 38. Spring 58 engages a proximal end 60 of driver 50. A proximal end 62 of spring 58 abuts a support 64 formed in upper housing 42. In order to control the movement of driver 50 within obturator housing 38, a guide 66 is provided on lower housing 44 and includes a longitudinally extending slot 68. Driver 50 is provided with a tab 70 which rides within slot 68. Thus, guide 66 controls the longitudinal motion of driver 50 within obturator housing 38.

In order to puncture tissue, such as, for example, the wall of a body cavity, obturator assembly 14 is provided with an elongate obturator member 72 having a cutting blade 74 positioned on a distal end 76 of obturator member 72. A pair of longitudinally extending arms 78a and 78b are provided on distal end 76 of obturator member 72 to secure cutting blade 74 thereon. A shield nose 80 and a support tube 82 are associated with obturator assembly 14 and are provided to shield blade 74 when not in use. A proximal end 84 of shield nose 80 is affixed to a distal end 86 of support tube 82 by any of various known means, such as, for example, crimping, welding, gluing, etc. A proximal end 88 of support tube 82 is fixedly secured to support 64 in upper housing 42.

Shield nose 80 is provided with a truncated cavity 90 for receipt of cutting blade 74. Shield nose 80 is further provided with a blunt tip 92 to prevent injury to organs underlying the wall of a body cavity during insertion therethrough.

In order to move obturator member 74 within support tube 82, and thus move cutting blade 74 within shield nose 80, a plunger 94 is provided through upper housing 42. Plunger 94 includes a handle 96 and a tube 98 extending distally from handle 96. Tube 98 extends through a plunger hole 100 formed within upper housing 42. A proximal end 102 is affixed within a bore 104 formed within tube 98. A spring 106 is provided about proximal end 102 of obturator member 72 to bias obturator member 72 within support to 82. Thus, cutting blade 74 is biased proximally within truncated cavity 90 of shield nose 80.

It should be noted that, while support tube 82 and shield nose 80 are illustrated as being fixed relative to obturator housing 38 and obturator member 72 and cutting blade 64 are disclosed as being movable relative to obturator housing 38, it is within the contemplated scope of the present disclosure that obturator member 72 and cutting blade 64 may be fixed relative to obturator housing 38 and shield nose 80 and support tube 82 movably mounted relative to obturator housing 38. In this situation, tissue pressure against shield nose 80 will allow shield nose 80 and support tube 82 to move proximally, against the bias of spring 106, relative to cutting blade 64 to expose cutting blade 64 to tissue. Upon the release of pressure against shield nose 80, shield nose 80 than advances distally against the bias of spring 106 to go cover and shield cutting blade 64 from exposure to underlying tissues.

In certain situations, it is desirable to provide electrocautery features to obturator assembly 14 and, specifically to cutting blade 74. Thus, an electrical conduit 108 is provided on upper housing 42 and is in electrical connection with obturator member 72 as described in more detail hereinbelow. Where electrocautery features are desired, obturator member 72 may be formed of a conductive material or, may be formed of a non-conductive material having a conductive inner core for transmission of electrical power to cutting blade 74.

Figure 3A:
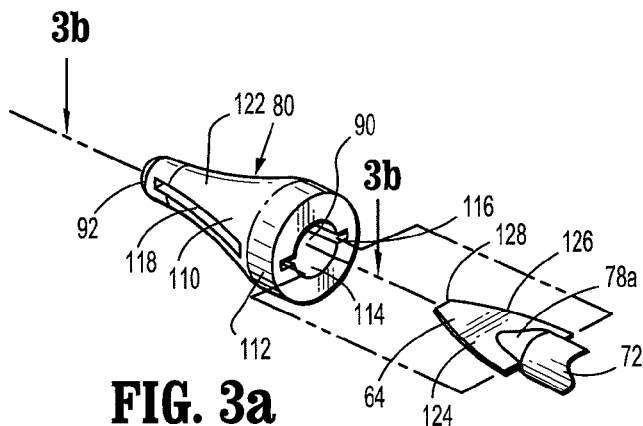
FIG. 3a is an enlarged area of detail view of FIG. 3.
Figure 3B:
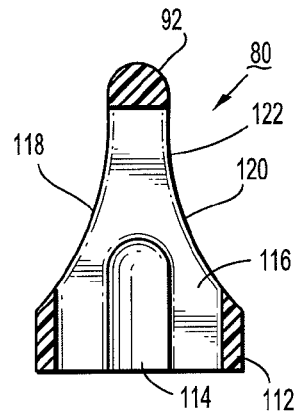

Referring now to FIGS. 3a and 3b, shield nose 80 includes a conical, concave center section 110 extending proximally from blunt tip 92. Shield nose 80 additionally includes a generally cylindrical proximal end 112. As noted hereinabove, shield nose 80 is provided with a truncated cavity 90 for receipt of cutting blade 64. Specifically, truncated cavity 90 generally includes a cylindrical center portion 114 which intersects a planner portion 116. Cylindrical portion 114 is configured to receive distal end 76 and arms 78a and 78b of obturator member 72 while planner portion 116 receives and supports cutting blade 64. A pair of slots 118 and 120 or formed through a side surface 122 of conical concave center section 110 of shield nose 80.

Referring specifically to FIG. 3a, cutting blade 64 is generally planner and includes a pair of sharp convex cutting side edges 124 and 126. Cutting blade 64 terminates in a blunt atraumatic truncated tip 128.

Figure 4:
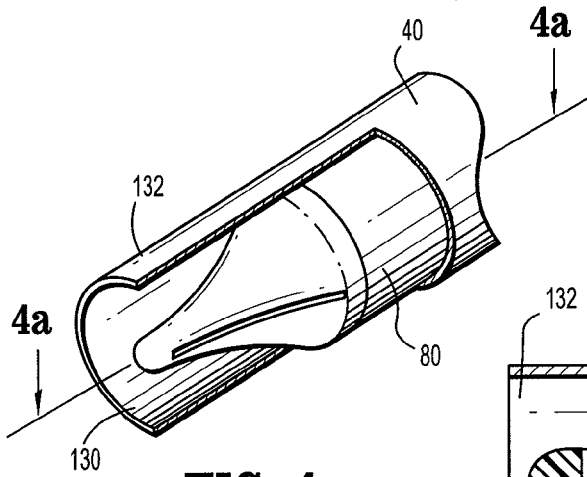
FIG. 4 is a perspective view, partially shown in section, of an shield nose of the obturator assembly in a retracted position within a safety shield of the obturator assembly.
Figure 4A:
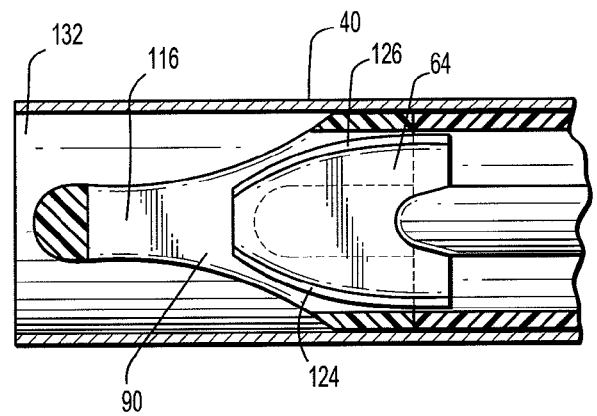
FIG. 4a is a cross sectional view taken along line 4a-4a of FIG. 4.

Referring to FIG. 4a, shield nose 80 is illustrated within a bore 130 of safety shield 40. Specifically, in the assembled condition, shield nose 80 is initially positioned within bore 130 at a distal end 132 of safety shield 40.

Referring to FIGS. 4 and 4a, when cutting blade 64 is in a proximal-most position within shield nose 80, cutting side edges 124 and 126 are proximal within planner portion 116 of truncated cavity 90. Thus, cutting side edges 124 and 126 are shielded from contact with surrounding body tissue when cutting blade 64 is in the proximal most position within truncated cavity 90 of shield nose 80.

Figure 5:
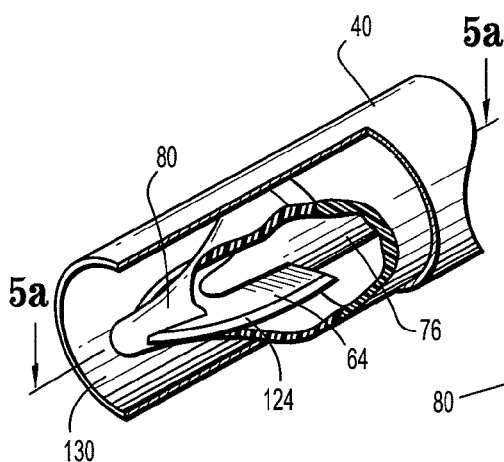
FIG. 5 is a perspective view, partially shown in section, of the shield nose with a cutting blade of the obturator tip in an extended position.
Figure 5A:
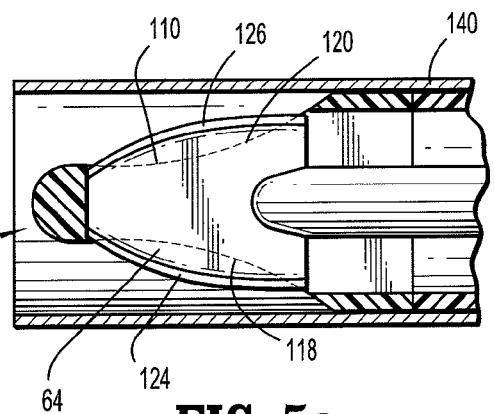
FIG. 5a is a cross-sectional view taken along line 5a-5a of FIG. 5.

Similarly, with reference to FIGS. 5 and 5a, when cutting blade 64 is in a distal most position within shield nose 80, cutting side edges 124 and 126 of cutting blade 64 project through slots 118 and 120 formed through side surface 122 of conical concave center section 110 of shield nose 80 and are in a position to cut tissue.

Figure 6:
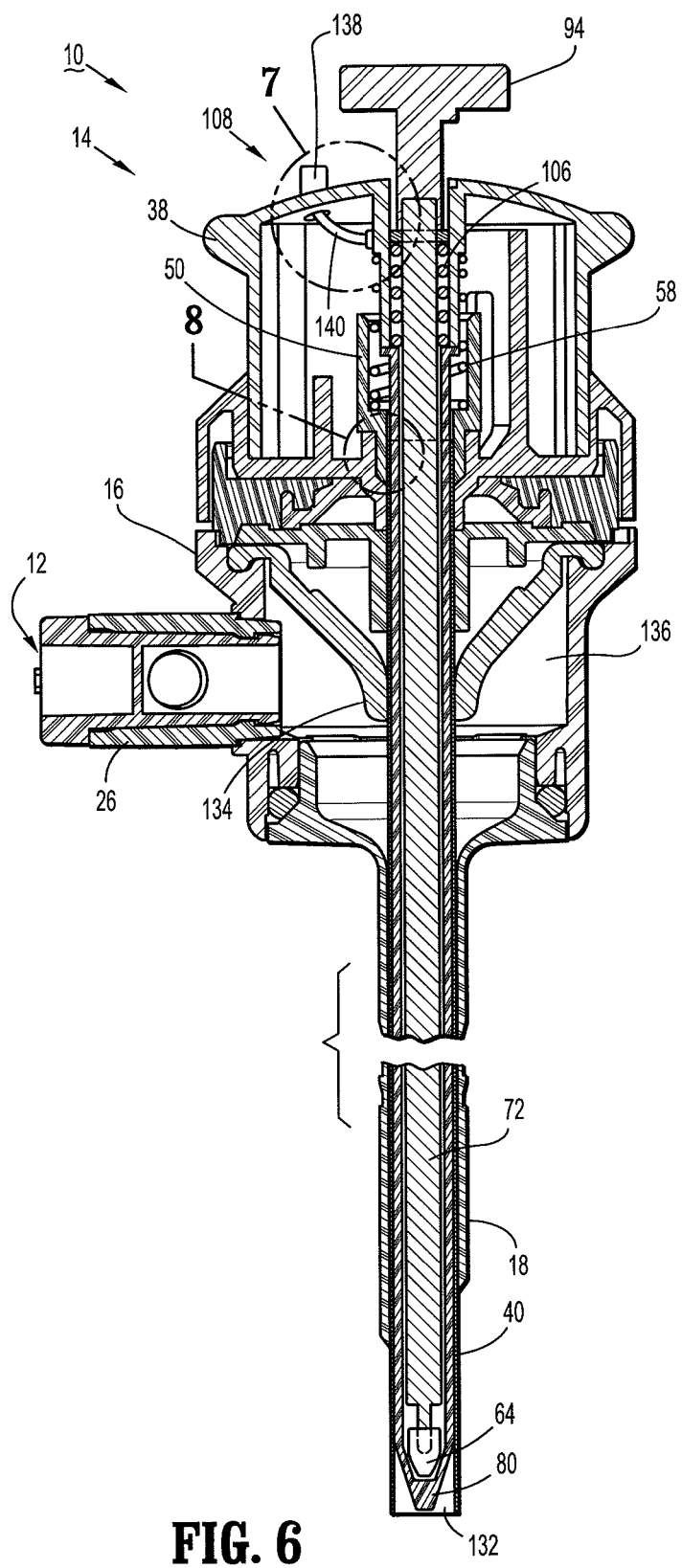
FIG. 6 is a cross-sectional view of the trocar assembly of FIG. 1.

Referring now to FIG. 6, as noted hereinabove, cannula assembly 12 includes a valve 26 for receipt of a source of insufflation fluid. In order to prevent the escape of insufflation fluid out of cannula assembly 12, cannula assembly 12 is provided with a duckbill valve 134 located within an interior 136 of cannula housing 16. Duckbill valve 134 is in a normally closed position and is provided to seal about safety shield 40 when obturator assembly 14 is inserted through cannula assembly 12.

Figure 7:
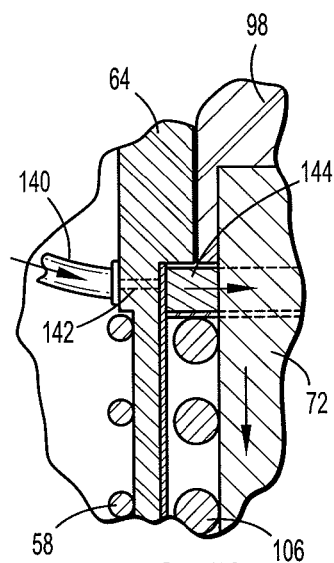
FIG. 7 is an enlarged area of detail view of FIG. 6.

Referring for the moment to FIGS. 6 and 7, as noted hereinabove it is often desirable to provide an obturator assembly with electrocautery features. Cannula assembly 12 includes electrical conduit 108. With reference to FIG. 6, electrical conduit 108 generally includes a connector 138 affixed to upper housing 38 and a cable 140 extending from connector 138 to obturator member 72. With specific reference to FIG. 7, a wire 142 extends from cable 140 and passes through support 64 in upper housing 42. A wiper 144 is affixed to wire 142 and is in electrical contact with obturator member 72. Thus, by providing a source of electrical power to electrical conduit 108, the power is passed through obturator member 72 to cutting blade 64 (FIG. 6) for providing electrocautery action on the tissue being operated upon.

Figure 8:
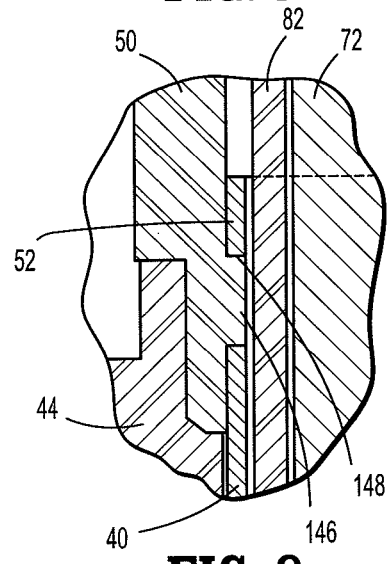
FIG. 8 is enlarged area of detail view of FIG. 6.

With reference to FIG. 8, and as noted hereinabove, safety shield 40 is affixed to driver 50. Specifically, driver 50 is provided with one or more tabs 146 which are configured to reside within slots 148 formed in proximal end 52 of safety shield 40. (See also FIG. 3).

Referring now to FIGS. 6 and 9-12, the operation of trocar assembly 10 and, specifically obturator assembly 14 will now be described. Referring initially to FIG. 6, in the assembled condition of trocar assembly 10, obturator assembly 14 is inserted through cannula assembly 12. Specifically, safety shield 40 and obturator member 72 of obturator assembly 14 are inserted through cannula housing 16 and cannula sleeve 18. Duckbill valve 134 provided within interior 136 of cannula housing 16 seals about safety shield 40. Plunger 94 is in the proximal most positioned against the bias of spring 106 to position cutting blade 64 in the proximal most position within shield nose 80. As shown, shield nose 80 and cutting blade 64 are in a proximal position within distal end 132 of safety shield 40. (See also FIGS. 4 and 4a).

Figure 9:
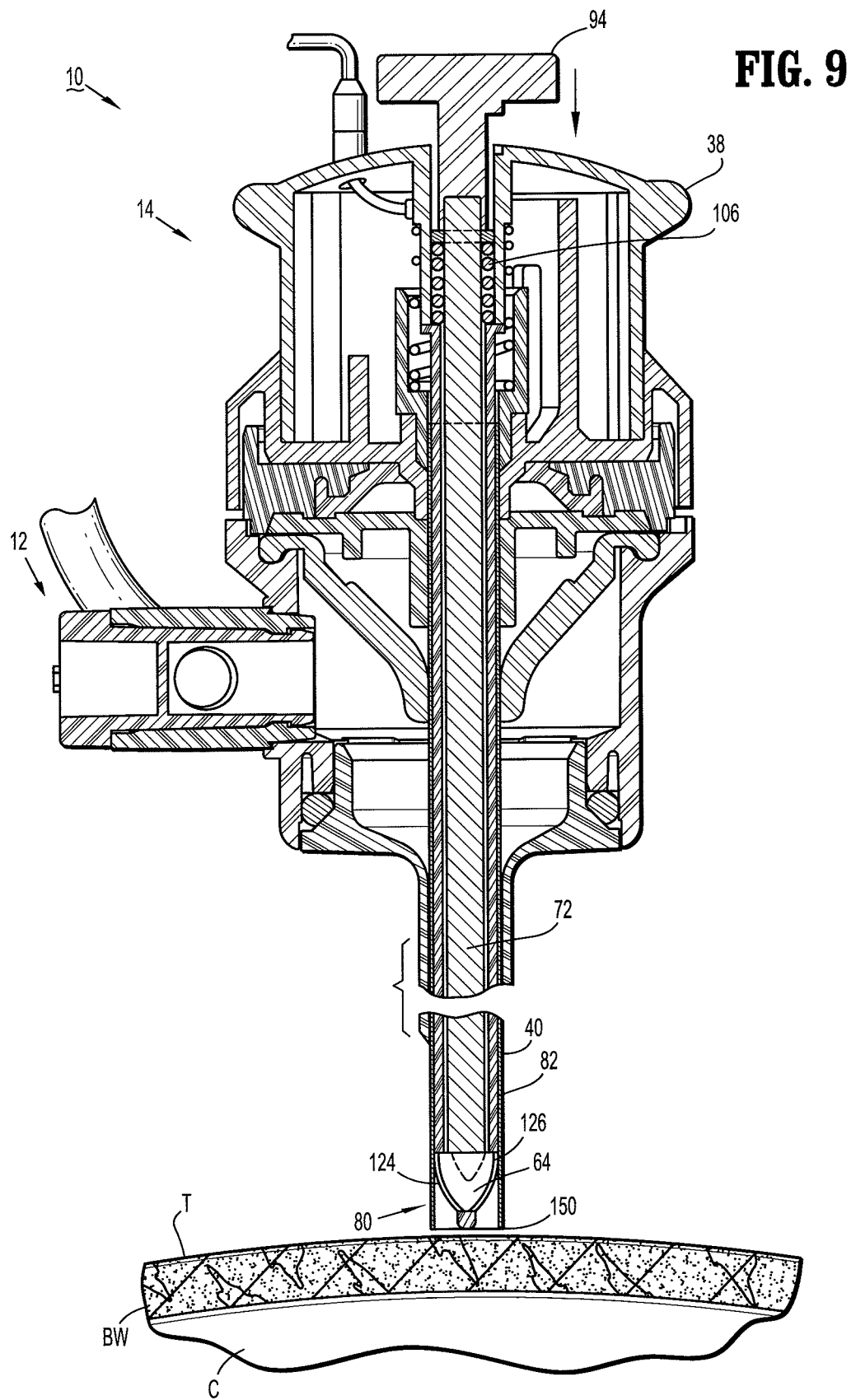
FIG. 9 is a cross-sectional view of the trocar assembly, positioned adjacent tissue, illustrating extension of the cutting blade within the shield nose.

With reference to FIG. 9, in use, trocar assembly 10 is positioned adjacent a tissue T such as an abdominal wall such that a distal end 150 of safety shield 40 abuts a body wall BW of tissue T. A cavity C exists beneath body wall BW and contains the desired organs to be operated upon (not shown). Initially, plunger 94 is depressed against the bias of spring 106 to drive obturator member 72 distally relative to support tube 82. Cutting blade 64 it is advance to the proximal most positioned within shield nose 80 to expose convex cutting edges 124 at 126 of cutting blade 64 through shield nose 80. (See also FIGS. 5 and 5a).

Figure 10:
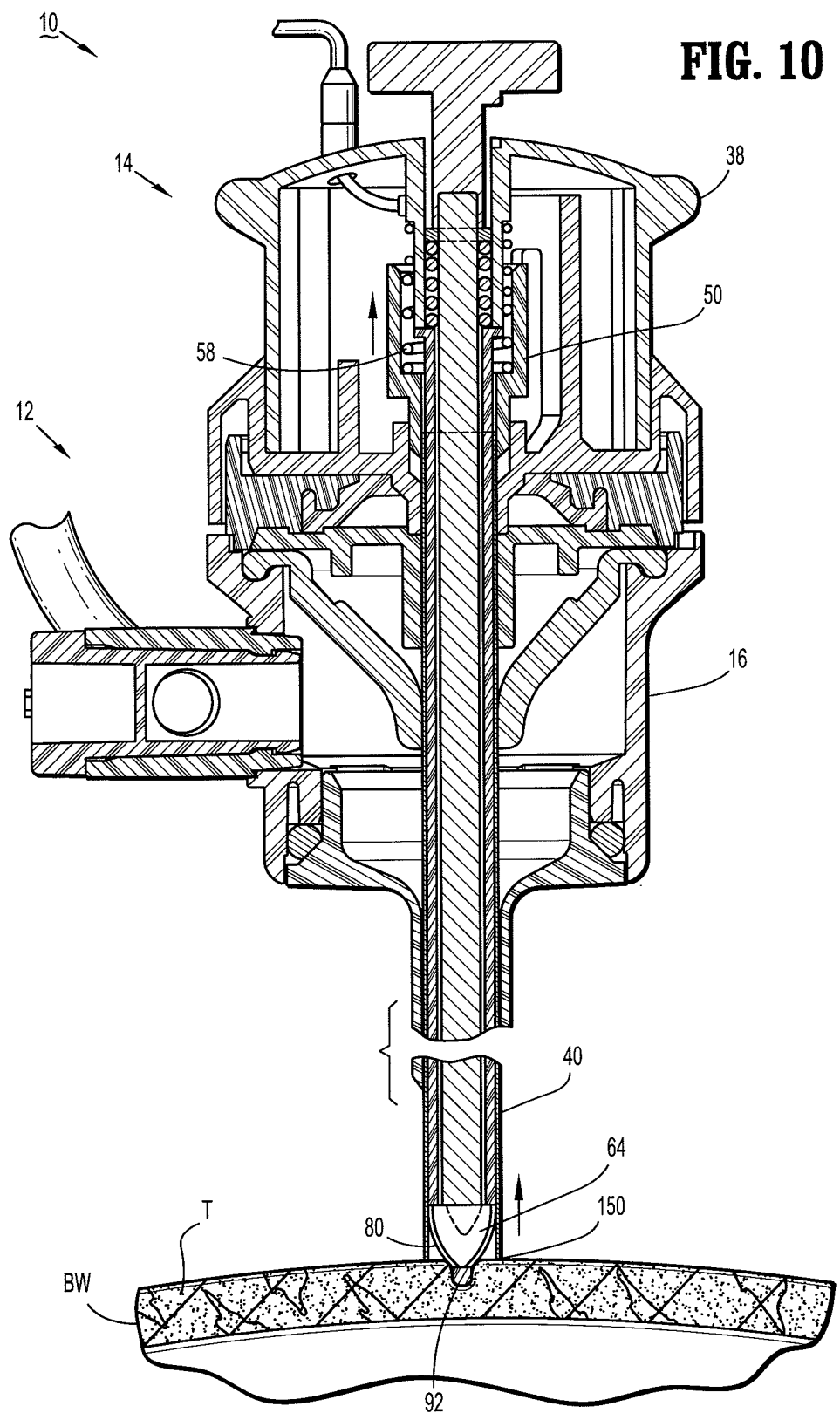
FIG. 10 is a cross-sectional view of the trocar assembly during initial urging of the trocar assembly against the tissue to retract the safety shield.

Referring now to FIG. 10, once cutting blade 64 has been exposed through shield nose 80, trocar assembly 10 as a whole can be advanced against body wall BW of tissue T. Specifically, distal end 150 of safety shield 40 engages body wall BW and is driven proximally relative to obturator housing 38 and against the bias of spring 58. This begins to expose cutting blade 64 to body wall BW of tissue T. As shown, blunt tip 92 of shield nose 80 engages body wall BW. As noted hereinabove, blunt tip 92 is provided to prevent cutting of underlying tissues as cutting blade 64 creates an incision and passes through body wall BW.

Figure 11:
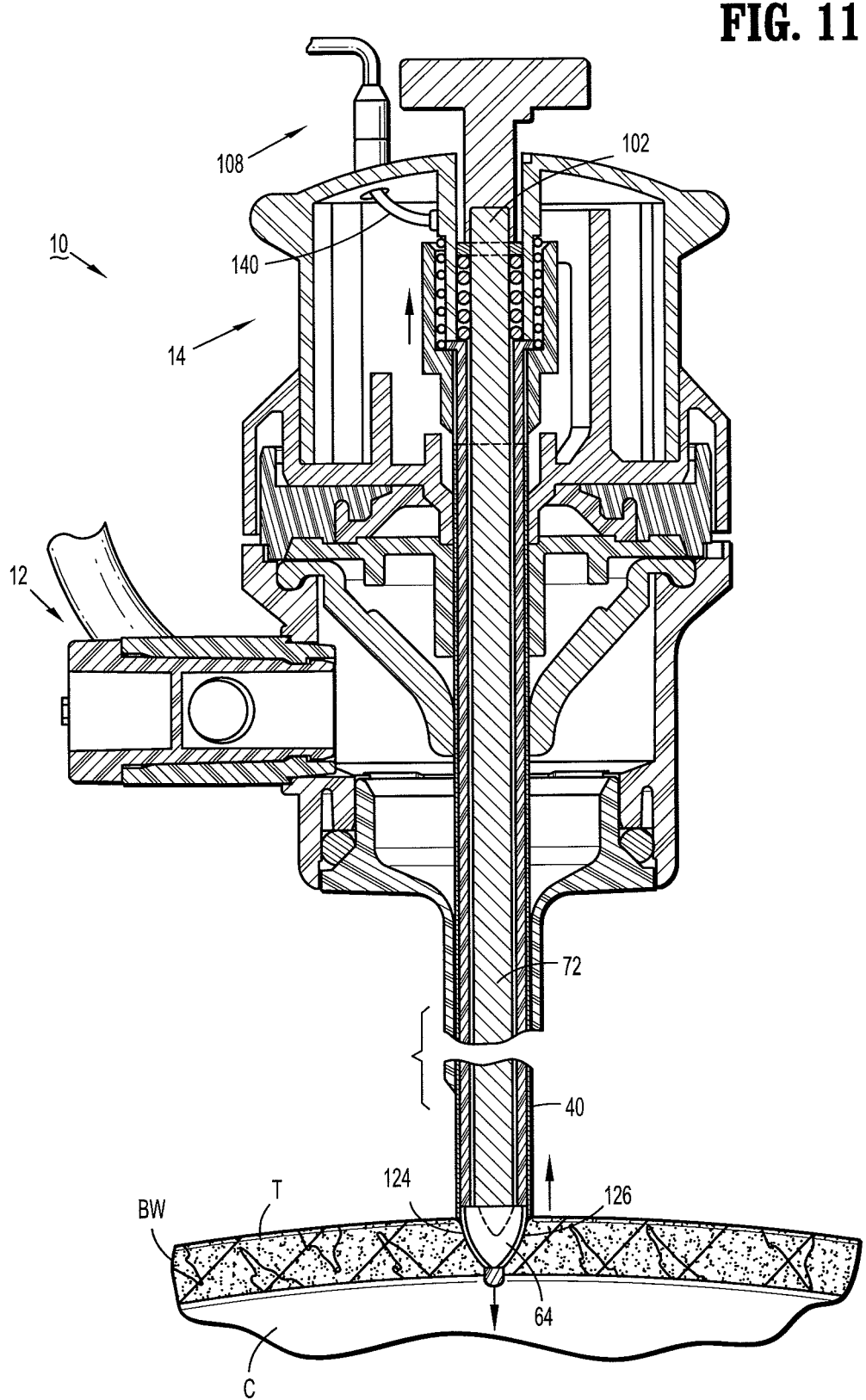
FIG. 11 is a cross-sectional view of the trocar assembly during penetration of the tissue by the shield nose and cutting blade.

As best shown in FIG. 11, as trocar assembly 10 is further urged against body wall BW, convex cutting edges 124 and 126 of cutting blade 64 cut into, and create an incision through, body wall BW of tissue T to provide access to cavity C. As noted hereinabove, it is often desirable to provide electrocautery action to cutting blade 64 to facilitate cutting through body wall BW. Thus, by providing a source of power to electrical conduit 108, power is passed through cable 140 to proximal end 102 of obturator member 72. As further noted hereinabove, obturator 72 may be formed completely of a conductive material or may be formed of a non-conductive material having a conductive inner core in electrical connection with 64. In this monopolar type system cutting blade 64 is energized to facilitate cutting through body wall BW and assist in cauterizing the sides of the incision therethrough.

Figure 12:
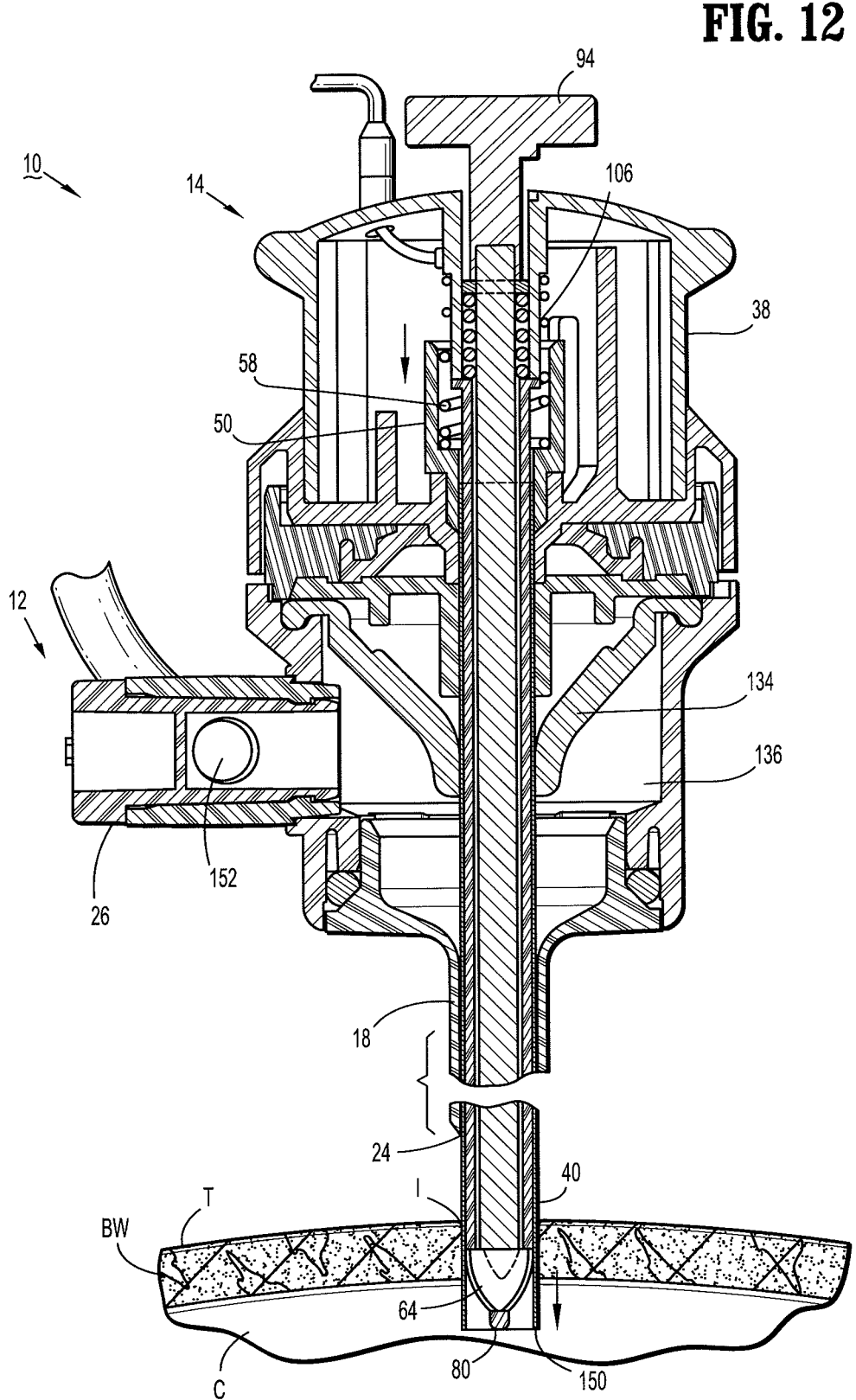
FIG. 12 is a perspective view of the trocar assembly after penetration of the tissue and advancement of the safety shield to cover the cutting blade.

Referring to FIG. 12, once cutting blade 64 has created an incision I through body wall BW, safety shield 40 is driven through incision I due to the bias of spring 58 against driver 50 connected to safety shield 40. In this manner, exposed cutting blade 64 is shielded from any underlying organs to prevent damage thereto. Alternatively, and or in addition to, pressure may be released from plunger 94 to allow cutting blade 64 to retract within shield nose 80 due to the bias of spring 106. In this manner, cutting blade 64 is safely contained within shield nose 80 to prevent damage to underlying tissues.

It will be understood that various modifications may be made to the embodiments disclosed herein. For example, as noted hereinabove, the obturator member in cutting blade may be fixed relative to the obturator housing while the shield nose and support tube bias distally relative to the cutting blade. Further, the cutting blade may assume other configurations than planer such as, for example, triangular, etc. with corresponding openings in the shield nose to allow exposure of the cutting blade. Additionally, various internal components of the obturator assembly may be formed of nonconductive materials when electrocautery features are provided to the cutting blade. Therefore, the above description should not be construed as limiting, but merely as exemplifications of particular embodiments. Those skilled in the art will envision other modifications within the scope and spirit of the claims appended hereto.

The invention claimed is:

1. An obturator assembly comprising:
   an obturator housing;
   a support tube extending distally from the obturator housing;
   a shield nose affixed to a distal end of the support tube, the shield nose defining a truncated cavity and having a concave center portion on an outer surface thereof;
   an obturator member movably mounted relative to the support tube;
   a cutting blade having at least one cutting edge and a truncated tip, the cutting blade being affixed to a distal end of the obturator member and being movable within the truncated cavity of the shield nose, wherein the shield nose has at least one slot formed through the concave center portion and in communication with the truncated cavity for allowing passage of the at least one cutting edge therethrough; and
   a safety shield biasedly mounted to the obturator housing between an advanced position wherein the safety shield is received about the shield nose and a retracted position wherein the safety shield is moved from about the shield nose.

2. The obturator assembly as recited in claim 1, wherein the shield nose has a blunt tip distal of the truncated cavity.

3. The obturator assembly as recited in claim 1, wherein the truncated cavity includes a planar portion for receipt of the cutting blade.

4. The obturator assembly as recited in claim 1, wherein the truncated cavity includes a cylindrical portion for receipt of the distal end of the obturator member.

5. The obturator assembly as recited in claim 1, further comprising a spring positioned between the obturator housing and the obturator member, the spring biasing the obturator member proximally relative to the support tube.

6. The obturator assembly as recited in claim 5, further comprising a plunger affixed to a proximal end of the obturator member.

7. The obturator assembly as recited in claim 1, further comprising an electrical conduit attached to the obturator housing and in electrical connection with the cutting blade.

8. The obturator assembly as recited in claim 7, wherein the obturator member is formed of an electrically conductive material.

9. The obturator assembly as recited in claim 7, wherein the obturator member is formed of an electrically nonconductive material and includes an electrically conductive inner core.

10. The trocar assembly as recited in claim 1, wherein the truncated tip of the cutting blade is blunt.

11. The trocar assembly as recited in claim 1, wherein the truncated tip of the cutting blade is atraumatic.

12. The trocar assembly as recited in claim 1, wherein the truncated tip is solid.

13. An obturator assembly comprising;
    an obturator housing;
    a support tube extending distally from the obturator housing;
    a shield nose affixed to a distal end of the support tube, the shield nose having a conical center portion and defining a cavity;
    an obturator member movably mounted relative to the support tube;
    a cutting blade having at least one cutting edge and a distal region, the cutting blade being affixed to a distal end of the obturator member and movable within the cavity such that when the cutting blade is in its distal-most position, the distal region of the cutting blade remains within the cavity of the shield nose; and
    a safety shield biasedly mounted to the obturator housing such that the safety shield extends over the shield nose to prevent the shield nose from being exposed unless a force is applied to the safety shield.

14. The obturator assembly as recited in claim 13, further comprising a spring engageable with the safety shield to bias the safety shield distally relative to the obturator housing.

15. The obturator assembly as recited in claim 14, further comprising a driver engageable with the spring and affixed to a proximal end of the safety shield.

16. The obturator assembly as recited in claim 15, further comprising a guide formed in the obturator housing and a tab formed on the driver and movable within the guide.

17. The obturator assembly as recited in claim 13, wherein, the shield nose has a concave center portion and at least one slot formed through the concave center portion and in communication therewith for allowing passage of the at least one cutting edge therethrough.

18. A trocar assembly comprising;
    a cannula assembly including a cannula housing and a cannula sleeve extending distally from the cannula housing; and
    an obturator assembly insertable through the cannula assembly and including:
      an obturator housing;
      a support tube extending distally from the obturator housing;
      a shield nose affixed to a distal end of the support tube, the shield nose defining a cavity and having a blunt distal end and a proximal-facing surface;
      an obturator member movably mounted relative to the support tube;
      a cutting blade having at least one cutting edge and a distal region, the cutting blade affixed to a distal end of the obturator member and movable within the cavity, wherein when the cutting blade is in its distal-most position, the distal region of the cutting blade engages the proximal-facing surface of the shield nose so as to prevent the distal region of the cutting blade from being exposed; and
      a safety shield movably mounted to the obturator housing so as to selectively expose the shield nose.

19. The trocar assembly as recited in claim 18, wherein the cannula housing includes a valve positioned within an interior of the cannula housing such that the valve seals about the safety shield when the obturator assembly is inserted into the cannula assembly.

* * * * *